US00PP22827P2

(12) United States Plant Patent
Kordes

(10) Patent No.: US PP22,827 P2
(45) Date of Patent: Jul. 3, 2012

(54) FLORIBUNDA ROSE PLANT NAMED 'KORKOSIEB'

(50) Latin Name: *Rosa hybrida*
Varietal Denomination: KORkosieb

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,241

(22) Filed: Oct. 14, 2010

(51) Int. Cl.
*A01H 5/00* (2006.01)

(52) U.S. Cl. ..... Plt./150

(58) Field of Classification Search ..... Plt./151, Plt./150, 139, 140
See application file for complete search history.

*Primary Examiner* — June Hwu

(57) ABSTRACT

A new and distinct variety of rose with long lasting, novel cherry red flowers, and attractive foliage with good disease resistance. It exhibits compact, erect growth with abundant flowers. The new variety propagates well by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORkosieb'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1997. The crossing was between an unnamed seedling and 'KORparesni', an unpatented rose from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORkosieb'.

SUMMARY OF THE INVENTION

The new rose plant may be distinguished from its seed parent, an unnamed seedling, by the following combination of characteristics:

1. 'KORkosieb' has a moderately strong fragrance. The unnamed seedling has a light fragrance.
2. Petal count for 'KORkosieb' is, on average, 60. Petal count for the unnamed seedling is, on average, 20.

The new rose plant may be distinguished from its pollen parent, 'KORparesni', by the following combination of characteristics:

1. 'KORkosieb' has a moderately strong fragrance. 'KORparesni' has a light fragrance.

2. Petal count for 'KORkosieb' is, on average, 60. Petal count for 'KORparesni' is, on average, 30.
3. 'KORkosieb' exhibits better disease resistance than the pollen parent.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORkosieb' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORkosieb' was selected in May, 1998 from the seedling beds to be asexually propagated for further evaluation. The first asexual propagation of 'KORkosieb' was done by budding to seedling understocks in July, 1998 at the inventor's nursery in Offenseth-Sparrieshoop, Germany.

This initial and other subsequent propagations conducted in controlled environments demonstrate that 'KORkosieb' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORkosieb'.

DETAILED BOTANICAL DESCRIPTION

The following is a description of 'KORkosieb', as observed growing in July, 2009 in a nursery in Sparrieshoop, Germany on plants of 1 year of age. Subsequent observations were made in October, 2010 in Jackson County, Oreg. on plants of 1 year of age. Color references are made using The Royal Horticultural Society (London, England) Colour Chart, 2001 except where common terms of color are used.

For a comparison, several physical characteristics of the rose variety 'KORorbe', a non-patented rose variety from the same inventor are compared to 'KORkosieb' in Chart 1.

CHART 1

| Characteristic | 'KORkosieb' | 'KORorbe' |
|---|---|---|
| Petal count | 60 petals | 20-30 petals |
| Flowers per stem | 8-12 | 5-6 |
| General tonality of open flower | Red Group 50A | Red Group 38B |

Parents:

*Seed parent*.—An unnamed seedling.

*Pollen parent*.—'KORparesni'.

Classification:

*Botanical classification*.—*Rosa hybrida,* 'KORkosieb'.

*Commercial classification*.—Floribunda rose.

FLOWER AND FLOWER BUD

Blooming habit: Recurrent.

Flower bud:

*Size*.—Upon opening, 20 mm in length from base of receptacle to end of bud and 13 mm diameter at its widest point.

*Bud form*.—Medium. Pointed ovoid.

*Bud color*.—As sepals first unfold, bud color is Red-Purple Group 63A. When ¼ open, the upper surface of petals is Red-Purple Group 63C, and the lower surface is Red-Purple Group 63B.

*Sepals*.—Size: Average 22 mm long×9 mm wide. Shape: Sepals generally subulate. Sepal apex is generally cirrose. Weak foliaceous appendages on three of the five sepals. Base is flat at union with receptacle. Quantity: Five. Margins: With fine hairs and stipitate glands. Surface texture: Inner side: Covered in fine hairs. Outer surface: Smooth. Stipitate glands are present. Color: Upper surface Yellow-Green Group 147C. Lower surface Yellow-Green Group 144A, with intonations of Gray-Orange Group 178B.

Receptacle:

*Surface*.—Smooth, glabrous.

*Color*.—Yellow-Green Group 144A.

*Shape*.—Campanulate.

*Size:* 7 mm (h)×7 mm (w).

Pedicels:

*Surface*.—Smooth. With stipitate glands.

*Length*.—30 mm average length.

*Diameter*.—1-2 mm average diameter.

*Color*.—Yellow-Green Group 144A.

*Strength*.—Moderate.

*Borne*.—Most often 8-12 flower buds on pedicels per peduncle.

Peduncle:

*Surface*.—Smooth. With stipitate glands.

*Length*.—10-20 cm average length.

*Diameter*.—2.5-3.5 mm average diameter.

*Color*.—Yellow-Green Group 144A.

*Strength*.—Moderately stong.

Flower bloom:

*Fragrance*.—Light. Fruity.

*Duration*.—On the plant 6-8 days. As a cut flower, 4 to 6 days. Senesced petals clinging.

*Size*.—Medium flowered garden rose. When open, the average flower diameter is 55 mm and the average flower height is 30 mm.

*Form*.—Shape of flower when viewed from the side: Upon opening, upper part: Flat. Upon opening, lower part: Flattened convex. Open flower, upper part: Flat. Open flower, lower part: Flattened convex.

Color:

*Upon opening, petals*.—Outermost petals: Outer Side: Red Group 54B. Inner Side: Red Group 54B. Innermost petals: Outer Side: Red Group 54B. Inner Side: Red Group 57A.

*Upon opening, basal petal spots*.—Basal petal spot, outermost petals: Outer Side: Yellow Group 4B. Inner Side: Yellow Group 4B. Basal petal spot, innermost petals: Outer Side: Yellow Group 4B. Inner Side: Yellow Group 4B.

*After opening, petals*.—Outermost petals: Outer Side: Red Group 54A. Inner Side: Red Group 50A. Innermost petals: Outer Side: Red Group 54A. Inner Side: Red Group 50A.

*After opening, basal petal spots*.—Basal petal spot, outermost petals: Outer Side: Yellow Group 4B. Inner Side: Yellow Group 4B. Basal petal spot, innermost petals: Outer Side: Yellow Group 4B. Inner Side: Yellow Group 4B. Variegations: None.

General tonality: On open flower Red Group 50A to Red Group 50B. No change in the general tonality at the end of the 3$^{rd}$ day. Afterwards, general tonality is Red Group 51A.

Petals:

*Petal count*.—Approximately 60 petals under normal conditions.

*Petal reflex*.—Petals reflex slightly at opening.

*Petal edge*.—Entire.

*Petal shape*.—Rounded. Apex shape is round. Shape of base is rounded.

*Petal size*.—35 mm long; 30 mm wide.

*Thickness*.—Average.

*Petal arrangement*.—Generally in a regular pattern with overlapping edges.

Petaloids: Present.

*Petaloid count*.—Average of 1-2 per flower.

*Petaloid edge*.—Smooth.

*Petaloid texture*.—Smooth.

*Petaloid shape*.—Linear to elliptic.

*Petaloid size*.—Petaloids are 7 mm long and 4 mm wide.

*Petaloid color*.—Color of inner side is Red Group 52A. Color of outer side is Red Group 52A.

Reproductive organs:

*Pistils*.—Approximately 70-80 present. Stigmas: Location: Slightly superior in position to anthers. Color: Yellow Group 2B with intonations of Greyed-Purple Group 184B. Styles: Length: 9 mm long. Color: Yellow Group 2C.

*Stamens*.—Approximately 70-80 on average and regularly arranged. Anthers: Size: 1 mm long. Color: Yellow Group 12B. Pollen: Generally present. Color: Yellow Group 8A. Filaments: Color: Yellow Group 12D. Length: 9 mm.

THE PLANT

Plant growth: Vigorous. Compact, erect habit. When grown as a budded nursery plant the average plant height is 70 cm and the average plant width is 40 cm.

Stems:

*Stem color*.—Young wood: Yellow-Green Group 146D with intonations of Greyed-Red Group 181A. Older wood: Yellow-Green Group 147B.

*Stem surface*.—Young wood: Smooth. Older wood: Smooth.

Prickles: Present.

*Incidence*.—6-8 per 10 cm of stem.

*Size*.—Average length: 10 mm.

*Color*.—Immature prickles: Gray-Yellow Group 160A. Mature prickles: Gray-Red Group 181A. Senescing to Gray-Yellow Group 160B.

*Shape*.—Concave.

*Anthocyanin*.—Color Gray-Red Group 181A.

Leaves and leaflets: Normally 5-7 leaflets on normal leaves in middle of the stem.

*Venation pattern*.—Pyramidal net pattern.

*Leaf size*.—140-150 mm (l)×120 mm (w).

*Quantity*.—Average.

*Texture*.—Upper side of leaflet: Semi glossy. Smooth. Leathery. Under side of leaflet: Matte. Smooth. Leathery.

*Color, mature foliage*.—Upper Leaf Surface: Yellow-Green Group 147A. Lower Leaf Surface: Yellow-Green Group 147B.

*Color, juvenile foliage*.—Upper Leaf Surface: Yellow-Green Group 147C. Lower Leaf Surface: Yellow-Green Group 146B.

*Anthocyanin intonation*.—Present. Intonations present on juvenile leaf margins and developing leaves. Color: Gray-Orange Group 176B.

Stipules:

*Size*.—20 mm long. 8 mm between the tips of the stipule. Main body of stipule 5 mm in width.

*Shape*.—Elongated. Winged.

*Stipule color*.—Yellow-Green Group 147A. Anthocyanin: Gray-Red Group 178B.

*Presence of stipitate glands*.—Present on margins.

*Margins*.—Serrated.

Petiole:

*Length*.—22 mm.

*Diameter*.—1 mm.

*Petiole color*.—Yellow-Green Group 154C. Anthocyanin present on juvenile tissue.

*Underneath*.—A few small prickles underneath.

*Stipitate glands*.—Limited numbers of stipitate glands on margins.

Petiole rachis:

*Length*.—50-55 mm.

*Diameter*.—1-1.5 mm.

*Color*.—Green Group 143A. Anthocyanin present on juvenile tissue.

*Margins*.—With stipitate glands.

*Prickles*.—A few small prickles underneath.

*Stipitate glands*.—Limited numbers of stipitate glands on margins.

Leaflets:

*Size*.—Average size of the terminal leaflet is 50-55 mm (l)×27-30 mm (w).

*Shape*.—Elongated. Base: Ovate. Apex: Acute.

*Margins*.—Serrated.

*Texture*.—Leathery.

Hips/seed formation: None observed.

Winter hardiness: To date, the variety has been grown successfully in Zone 5.

Disease resistance: Very good resistance to Powdery mildew (*Sphaerotheca pannosa*), rust (*Phragmidium* ssp.), and blackspot (*Diplocarpon rosae*) diseases under normal growing conditions.

I claim:

1. A new and distinct variety of rose plant, as described and illustrated herein.

* * * * *

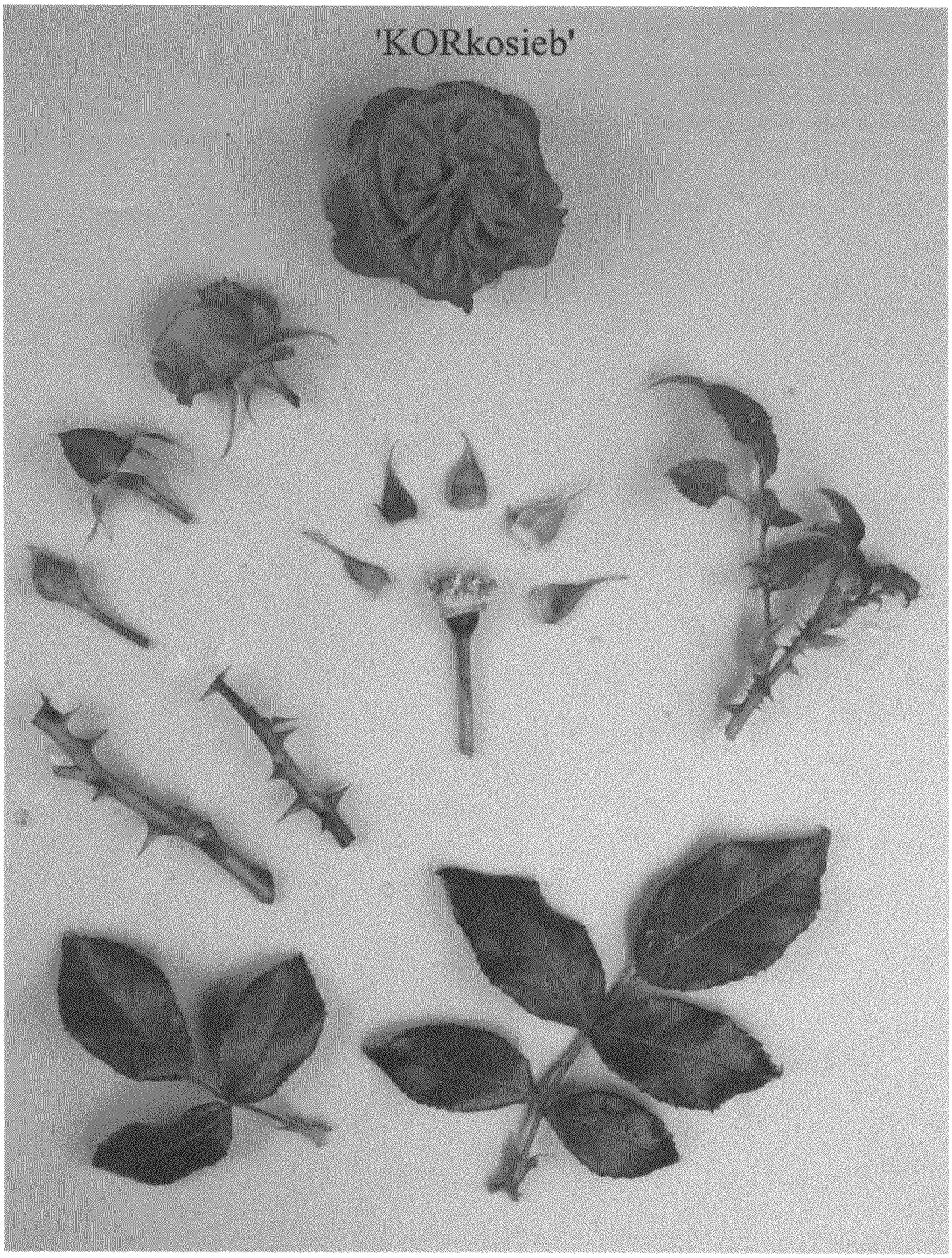
'KORkosieb'